United States Patent [19]
Barna

[11] Patent Number: 5,326,975
[45] Date of Patent: Jul. 5, 1994

[54] MEASUREMENT OF GAS LEAKS INTO GAS LINES OF A PLASMA REACTOR

[75] Inventor: Gabriel G. Barna, Richardson, Tex.

[73] Assignee: Texas Instruments Incorporated, Dallas, Tex.

[21] Appl. No.: 76,031

[22] Filed: Jun. 15, 1993

[51] Int. Cl.$^5$ .............................................. G01N 21/73
[52] U.S. Cl. ..................................... 250/372; 156/627; 204/192.13; 204/192.33; 204/298.03; 204/298.32
[58] Field of Search ............................. 250/336.1, 372; 156/626, 627, 345, 643; 204/192.13, 192.33, 298.03, 298.32

[56] References Cited

U.S. PATENT DOCUMENTS

| | | | |
|---|---|---|---|
| 4,415,402 | 11/1983 | Gelernt et al. | 156/626 |
| 4,493,745 | 1/1985 | Chen et al. | 156/345 X |
| 4,499,752 | 2/1985 | Fruzzetti et al. | 73/40.7 |
| 4,543,481 | 9/1985 | Zwick | 250/338.5 X |
| 4,851,683 | 7/1989 | Yang et al. | 250/339 |
| 4,883,560 | 11/1989 | Ishihara | 204/298.03 |

FOREIGN PATENT DOCUMENTS

| | | | |
|---|---|---|---|
| 58-30131 | 2/1983 | Japan | 156/626 |
| 62-180070 | 8/1987 | Japan | 204/298.03 |

*Primary Examiner*—Constantine Hannaher
*Assistant Examiner*—Edward J. Glick
*Attorney, Agent, or Firm*—Wade James Brady; Richard L. Donaldson

[57] ABSTRACT

A method for testing for gas leaks in plasma reactors and gas lines introducing gas into the reactor, includes: measuring the intensity of the plasma reactor light emission; introducing known increments of a test gas into the reactor; measuring the intensity of the plasma reactor light emission after each introduction of an increment of test gas into the reactor; producing a curve resulting from the intensity readings vs increments of introduced gas; and performing a regression analysis on the curve to determine a value of gas at which the intensity is equal to zero, which value of gas is the amount of gas that has been leaked into the reactor.

15 Claims, 3 Drawing Sheets

| | $O_2$/He (sccm) | Process sccm/gas | Leak sccm/gas | Measured sccm/gas | $R^2$ | Test |
|---|---|---|---|---|---|---|
| 1. | 50/100 | 100/$CF_4$ | 50/AIR | 53.1/AIR | 0.9998 | AIR |
| 2. | 50/100 | 100/$CF_4$ | 30/AIR | 28.1/AIR | 0.9967 | AIR |
| 3. | 50/240 | 200/$CF_4$ 210/$CHF_3$ | 14/AIR | 15.8/AIR | 0.9998 | AIR |
| 4. | 50/200 | 200/$CF_4$ 200/$CHF_3$ | 30/AIR | 30.0/AIR | 0.9965 | $N_2$ |
| 5. | 50/100 | 100/$CF_4$ | 30/$H_2$ | 29.3/$N_2$ | 0.9970 | $N_2$ |

MEASUREMENT OF GAS LEAKS INTO GAS LINES OF A PLASMA REACTOR

FIELD OF THE INVENTION

This invention relates to the measurement of gas leaks in gas lines, and more particularly to a method for the measurement of nitrogen or air leaks into the gas lines of a plasma reactor.

BACKGROUND OF THE INVENTION

Gas leaks into the main body of a plasma reactor are simple to detect. A "leakback" test will measure the leakage of gases into the evacuated process chamber. If all other gas sources are disconnected, it is obvious that the leak is due to air. But, a $N_2$ or air leak into the gas lines, the lines bringing the process gases to the reactor chamber, is a more difficult problem to diagnose and measure.

When such a problem is suspected, the appropriate gases are shut off at the source, the gas lines are evacuated and a "leakback" measurement is made on the "system" all the way back to the source. The problem with this technique is that gas supply lines, in a typical wafer fabrication lab, can be fifty to one hundred feet long. A complete evacuation and degassing of such a line can take many hours. Even then, it is sometimes difficult to determine if a particular leakback value on an evacuated line is due to a real leak, or a virtual leak due to the continued degassing of the line.

There are technical ways to analyze this problem. An RGA (Residual Gas Analyzer) will detect the concentration of $O_2$ or $N_2$ in any process gas. However, such apparatus is expensive, and is not routinely available in wafer fabrication labs, and has to be specifically hooked into the reactor.

Spectrophotometric techniques are other methods of testing. It is known that different species of gases, when excited by the plasma of the reactor, emit at specific wavelengths. In principle, the measurement of the intensity of the specific wavelength can be used to determine the amount of that species. In practice, spectral intensity measurements are readily obtained on most plasma reactors, as they are all equipped with "endpoint detectors". These are full spectrometers, or single-wavelength band-pass filters that are connected appropriately to measure the intensity of a specific wavelength.

While spectral intensity measurements are readily available, the determination of the concentration of species [X], from the intensity of the wavelength of X (I[X]), is not a straight forward matter. The problem is, that in addition to the concentration of [X], the value of I[X] at any particular time is a function of: the gain setting of the detector; the spectral transmittance of the window through which the I[X] measurement is made, this changes with the state of the reactor (residue buildup on the windows; and the other gases and pressure and RF conditions in the plasma so that there is no way to have a "standard calibration curve" of I[X] vs [X], and thus determine the magnitude of the leak of gas X into the process gas(es).

SUMMARY OF THE INVENTION

The invention is to a method for testing for gas leaks, particularly air and $N_2$ leaks into a plasma reactor. When an unknown quantity of unwanted gas is leaking into the reactor, this unknown quantity needs to be determined. In a test configuration of the invention, a gas leak of air or $N_2$ was introduced via a Mass Flow Controller calibrated for $N_2$ or air. The intensity of the plasma reaction light emission was measured. The signal measured was the intensity of the 334 run emission line ($I_{334}$) of a (50 cm He/100 He+$CF_4$ or $CHF_3$) plasma obtained via a 334 nm band-pass filter, and a photo diode set with a specific gain. Additional increments of known amounts or $N_2$ (or air) were added to the reactor and additional readings taken. A regression analysis on the $I_{334}$ vs [$N_2$] curve produced by the readings was performed. The resulting curve is monotonic, and may be represented by a quadratic relationship of the form: $I_{334} = a + b[N_2] + c[N_2]^2$. This equation is then solved for the value $I_{334} = 0$, where the resulting absolute value of [$N_2$] is the original amount of $N_2$ that has been continually leaking into the system.

The method for testing for gas leaks in plasma reactors and gas lines introducing gas into the reactor, includes the steps of: measuring the intensity of the plasma reaction light emission; introducing known increments of a test gas into the reactor; measuring the intensity of the plasma reaction light emission after each introduction of an increment of test gas into the reactor; producing a curve resulting from the intensity readings vs increments of introduced gas; and performing a regression analysis on the curve to determine a value of gas at which the intensity is equal to zero, which absolute value is the amount of gas that continues to leak into the reactor through the gas lines.

The technical advance represented by the invention as well as the objects thereof will become apparent from the following description of a preferred embodiment of the invention when considered in conjunction with the accompanying drawings, and the novel features set forth in the appended claims.

DESCRIPTION OF PREFERRED EMBODIMENT

The invention is to a method for detecting and measuring gas leaks into the gas lines of a process chamber, and more particularly into a plasma reactor. A technique exist that is called the "Standard Addition" method. This technique relies on the principle, illustrated in FIG. 1, that a calibration curve can be generated, "in situ", by the addition of "spikes" of a gas X into a test system containing a given amount of gas X. By extrapolating back to I[X]=0, the intercept absolute value is the original concentration of X in the test system.

The problem with this technique is that it is required and specified that the calibration curve must be linear over the range of concentrations employed. This is specifically not true for the problem solved by the present invention.

Figure 2:
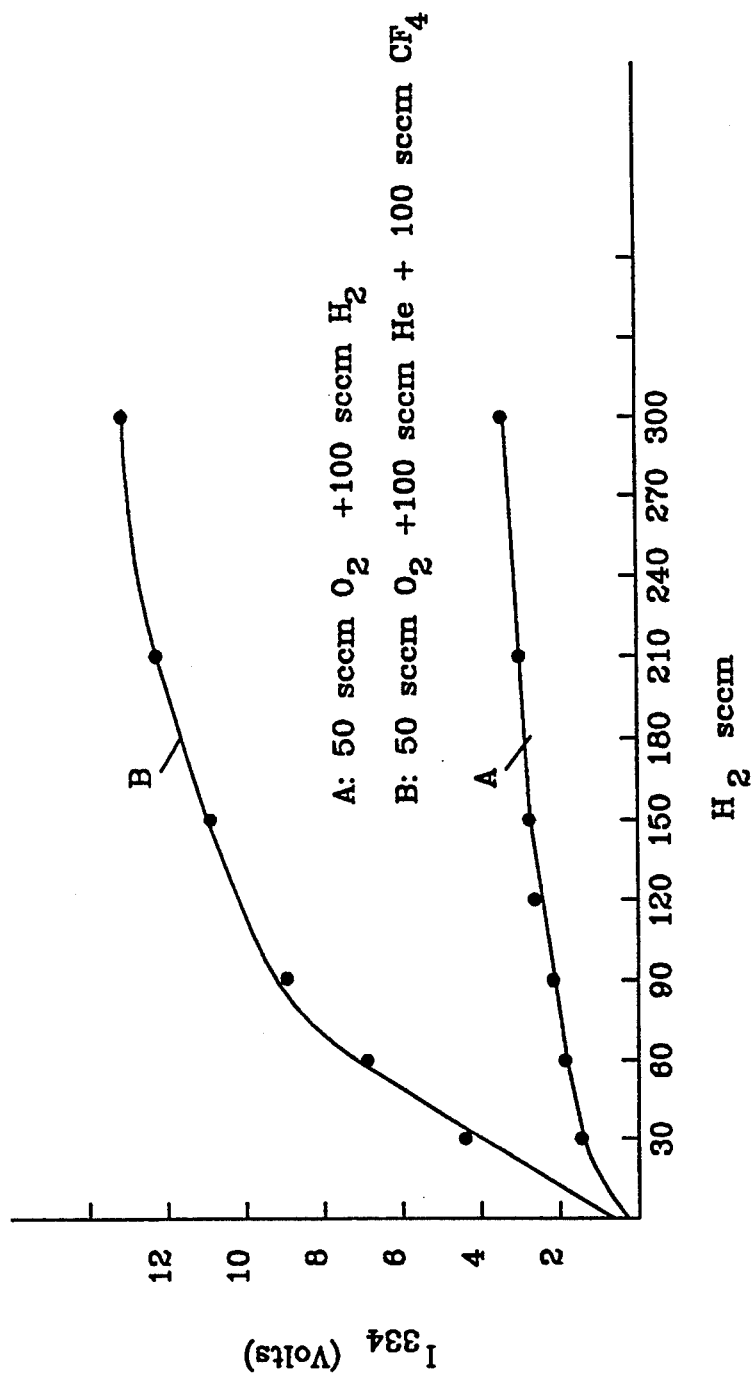
FIG. 2 illustrates the non-linearity of the relationships between $I_{334}$ and [$N_2$]

FIG. 2 illustrates the non-linearity of the relationships between $I_{334}$ and $[N_2]$. In Curve A the reactor contained 50 sccm $O_2$ + 100 sccm He. Increments of nitrogen were introduced in the quantities of 30, 60, 90, 150 and 210 sccm (standard cubic centimeters per minute). The result was curve A. The same quantities of $N_2$ were introduced into the reactor with the reactor containing 50 sccm $O_2$ + 100 sccm He + 100 sccm $CF_4$. The resulting curve B is quite different. The nonlinearity relationship between $I_{334}$ and $[N_2]$ prevents the use of the "Standard Addition" method in its classical, and usual, form.

It has been determined that a regression analysis on the $I_{334}$ vs $[N_2]$ curve, curves A and B FIG. 2, produced by the readings is monotonic, and may be represented by a quadratic relationship of the form: $I_{334} = a + b[N_2] + c[N_2]^2$. This equation is then solved for the value $I_{334} = 0$, where the resulting value of $[N_2]$, multiplied by $-1$, is the amount of $N_2$ that has been leaking into the system.

Figure 3A:
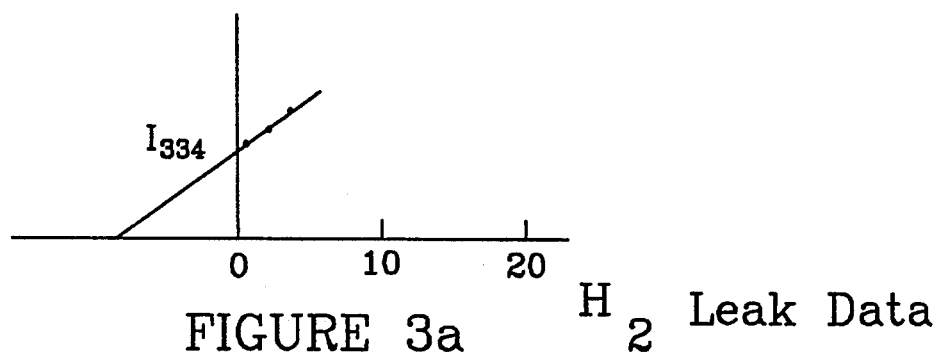
FIG. 3a shows a regression analysis of $I_{334}$ vs. nitrogen leak for small increments of added nitrogen.
Figure 3B:
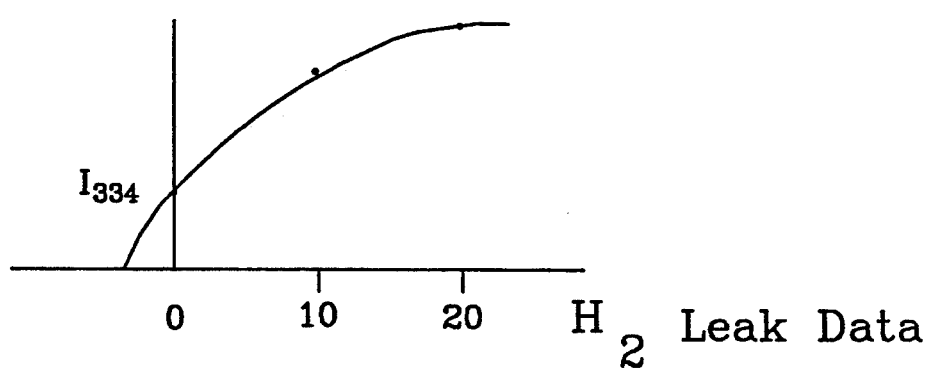
FIG. 3b shows a regression analysis of $I_{334}$ vs. nitrogen leak for larger increments of added nitrogen.

There are two factors related to the accuracy and the interpretation of the results of the test. A first basic consideration is that the results of the test relies on the extrapolation of data into a region where there is no data point. A possible source of error to be considered, related to the magnitude of the incremental steps, is the relative amount of $N_2$ to be added in the test cases. If the increments of test gas inserted into the reactor are small relative to the original amount, FIG. 3a, then the regression task is easier, but the extrapolation intercept at $I_{334} = 0$ is very dependent on the coefficients of regression. If the increments of injected gas are large relative to the original amount, FIG. 3b, then the regression becomes more inaccurate. The accuracy is maximized to about 5-10% of the absolute value when the incremental steps are similar to the "leak" value. For example, if the leak value is 30 sccm $N_2$, additions of 10, 20 and 30 sccm give the best accuracy. Where the total leak amount is unknown, as in the case of a real leak, then arbitrary magnitudes additions have to be first made. When the resulting extrapolation gives a value for $[N_2]$, the procedure is rerun with additions of injected gas more appropriately spaced.

A second consideration is that whether Air or $N_2$ is used for the standard addition steps. The resulting value should be considered in terms of an "$N_2$ equivalent" leak. This results from the fact that the procedure cannot distinguish between AIR (78% $N_2$) and pure $N_2$ as the source of the leak. As long as the result is considered in terms of a given $N_2$ leak rate, a judgement can then be made whether this rate (R) is from pure $N_2$ or from an R/0.78 rate of AIR leak.

Figures 4, 5:
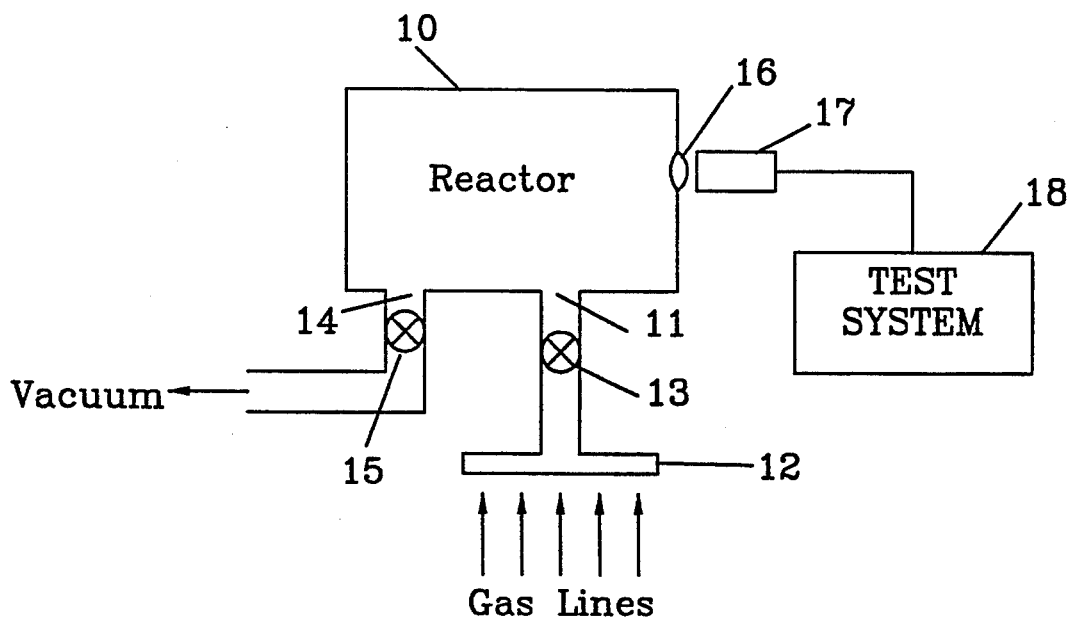
FIG. 4 is a tabulated data for leak test measurements.
FIG. 5 shows a test apparatus arrangement.

Experimental results are shown in FIG. 4. FIG. 4 is a tabulation of the flows of the basic $O_2$/He plasma (300 W RF, 2.0 torr), the Process gas in which the $N_2$ (or AIR) leak is presumably entrained, the rate and nature of the intentionally leaked gas, the rate and type (matched to the known type of the Leak gas) of the Measured leak, the $R^2$ value of the regression, and the type of Test gas used.

The tabulated data of FIG. 4 shows that the procedure can be run, with either AIR or $N_2$ as the test gas, with accuracies typically better than 10%. The demonstrated LOD (Limit of Detection) is 2%, but this is not the ultimate LOD.

Figure 1:
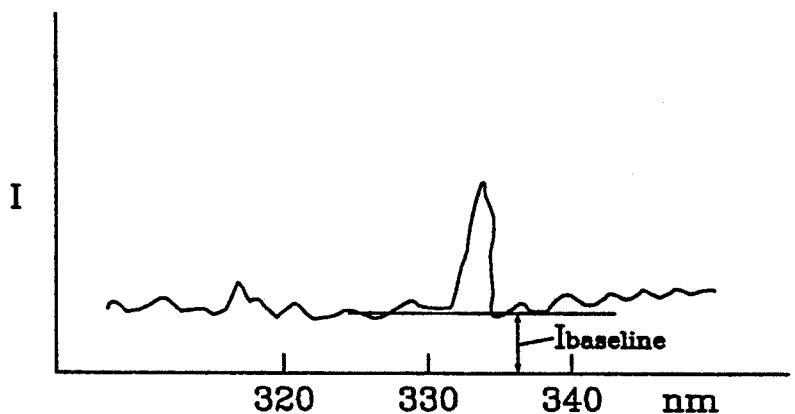
FIG. 1 is a typical spectral intensity vs. wavelength for a nitrogen containing plasma.

As far as the ultimate LOD is concerned, baseline correction has to be considered. This addresses the problem that the $N_2$ emission line is on top of a broadband plasma emission spectrum. As shown in FIG. 1, this means that the $I_{334}$ values, at any level of $[N_2]$, will be increased by $I_{baseline}$. Hence, even in the total absence of any $N_2$ in the system, the internal calibration will yield a "baseline equivalent nitrogen flow". This source of error can be eliminated if instead of a broad-band filter, a spectrometer is used for this procedure. Then, in addition to measuring $I_{334}$, the $I_{baseline}$ value can be measured at, for example, 320 and 340 nm. With the internal calibration then generated with the values of $(I_{334} - I_{baseline})$ vs. added $[N_2]$, the LOD can be significantly decreased.

The method of the invention can be utilized in any plasma reactor (etcher, deposition, uW, ECR . . . ) where gases are excited to an emitting state. In other non-plasma processing equipment, the method can be implemented by utilizing an "in-line" test cell. This test cell would have to provide its own RF excitation and spectral measurement capability. This procedure can be fully automated to provide continual unattended testing.

FIG. 5 illustrates a basic reactor system and emission detection system. Reactor 10 has a gas line input port 11 connected to a multi port gas manifold 12. Manifold 12 is capable of imputing different gases used in the reactor. Valve 13 is used to close off port 11.

A second port 14 is connected to a vacuum system that is used to evacuate the reactor. Valve 15 is used to close port 14.

A viewing window 16 is in the side of reactor 10. An emission intensity detector/spectrometer 17 views the plasma intensity in reactor 10, and supplies the intensity information to test system 18, which utilizes the intensity data and produces regression analysis used in detecting gas leaks in the reactor.

What is claimed is:

1. A method for testing for gas leaks in plasma reactors and gas lines introducing gas into the reactor, comprising the steps of:
   measuring the intensity of the plasma reaction light emission;
   introducing known increments of a test gas into the reactor;
   measuring the intensity of the plasma reaction light emission after each introduction of an increment of test gas into the reactor;
   producing a curve resulting from the intensity readings vs increments of introduced gas;
   performing a regression analysis on the curve to determine a value of gas at which the intensity is equal to zero, which value, multiplied by $-1$, of gas is the amount of gas that has been leaking into the reactor; and
   determining from the regression analysis whether there exists a gas leak.

2. The method according to claim 1, wherein the test gas introduced into the reactor is $N_2$.

3. The method according to claim 1, wherein the test gas introduced into the reactor is air.

4. The method according to claim 1, wherein the intensity of plasma emission light is measured at the 334 nm emission line.

5. The method according to claim 1, wherein the curve produced from the intensity readings vs increments of introduced gas is represented by the equation $I_{334} = a + b[N_2] + c[N_2]^2$.

6. The method according to claim 1, further including the steps of:

first determining an amount of gas that has been leaking into the reactor using increments of test gas of first increment amounts;

determining second increment amounts of test gas, said second increment amounts including amounts smaller than and approximately equal to said first determined amount of gas that has been leaking into the reactor; and repeating the method steps using increments of test gas of said second increment amounts to more accurately determine the amount of gas that has been leaking into the reactor.

7. The method according to claim 1, wherein said known increments of test gas are of increasing amounts with the amount of increase therebetween being the same.

8. A method for testing for gas leaks in plasma reactors and gas lines introducing gas into the reactor, comprising the steps of:

measuring the intensity of the plasma reaction light emission;

introducing known increments of a nitrogen containing test gas into the reactor;

measuring the intensity of the plasma reaction light emission after each introduction of an increment of test gas into the reactor;

producing a curve resulting from the intensity readings vs increments of introduced gas;

performing a regression analysis on the curve to determine a value of gas at which the intensity is equal to zero, which value, multiplied by −1, of gas is the amount of gas that has been leaking into the reactor; and determining from the regression analysis whether there exists a gas leak.

9. The method according to claim 8, wherein the test gas introduced into the reactor is air.

10. The method according to claim 8, wherein the intensity of plasma emission light is measured at the 334 nm emission line.

11. The method according to claim 8, wherein the curve produced from the intensity readings vs increments of introduced gas is represented by the equation $I_{334} = a + b[N_2] + c[N_2]^2$.

12. The method according to claim 8, further including the steps of:

first determining an amount of gas that has been leaking into the reactor using increments of test gas of first increment amounts;

determining second increment amounts of test gas, said second increment amounts including amounts smaller than and approximately equal to said first determined amount of gas that has been leaking into the reactor; and repeating the method steps using increments of test gas of said second increment amounts to more accurately determine the amount of gas that has been leaking into the reactor.

13. The method according to claim 8, wherein said known increments of test gas are stepped increments.

14. The method according to claim 8, wherein the test gas introduced into the reactor is $N_2$.

15. An apparatus for testing for and determining an amount of leaked gas in plasma reactors and gas lines introducing gas into the reactor utilizing plasma emission light, comprising:

a plasma reactor;

a detector for measuring the intensity of the plasma emission light;

means for injecting known amounts of a test gas into the plasma reactor; and a test system for recording the measured intensity of the plasma emission light prior to and each time an amount of test gas is injected into the plasma reactor, and for performing a regressive analysis on the measured intensity and injected amounts of test gas data to determine the amount of gas that has been leaking into the reactor.

* * * * *